US009009015B2

(12) United States Patent
Tanida (10) Patent No.: US 9,009,015 B2
(45) Date of Patent: Apr. 14, 2015

(54) FREE ENERGY DIFFERENCE ESTIMATION METHOD AND SIMULATION APPARATUS

(75) Inventor: Yoshiaki Tanida, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 570 days.

(21) Appl. No.: 13/366,856

(22) Filed: Feb. 6, 2012

(65) Prior Publication Data

US 2012/0239356 A1 Sep. 20, 2012

(30) Foreign Application Priority Data

Mar. 14, 2011 (JP) .................................. 2011-055828

(51) Int. Cl.
*G06G 7/58* (2006.01)
*G06F 19/00* (2011.01)
*G06F 19/16* (2011.01)

(52) U.S. Cl.
CPC .............. *G06F 19/701* (2013.01); *G06F 19/16* (2013.01); *G06F 19/706* (2013.01)

(58) Field of Classification Search
None
See application file for complete search history.

(56) References Cited

U.S. PATENT DOCUMENTS 6,368,813 B1 * 4/2002 Reznik et al. .................. 435/7.5
8,452,576 B2 * 5/2013 Reich et al. ....................... 703/5
2007/0061119 A1 3/2007 Shimada et al.
2008/0247991 A1 * 10/2008 Trout et al. ................... 424/85.4
2011/0130968 A1 * 6/2011 Clark .............................. 702/19

FOREIGN PATENT DOCUMENTS

JP 2007-080044 A 3/2007

OTHER PUBLICATIONS

Ajay Computational Methods to Predict Binding Free Energy in Ligand-Receptor Complexes Journal of Medicinal Chemistry, vol. 38, No. 26, pp. 4953-4967, Dec. 22, 1995.*
Johan Aqvist et al. A New Method for Predicting Binding Affinity in Computer-Aided Drug Design Protein Engineering vol. 7, No. 3, pp. 385-391, 1994.*

* cited by examiner

*Primary Examiner* — Omar Fernandez Rivas
*Assistant Examiner* — Cuong Luu
(74) *Attorney, Agent, or Firm* — Fujitsu Patent Center (57) ABSTRACT

In a free energy difference estimation method, the partial free energy difference indicates a bound state between a target compound and a first candidate compound bindable to the target compound, and is stored in a storage part for each value of a binding constant. A change region, in which a partial free energy difference is equal to or greater than a predetermined change value, is specified in a region of the binding constant. The partial free energy difference of a second candidate compound in the change region is interpolated based on the partial free energy difference acquired in each of a previous region and a following region by using an approximation function.

6 Claims, 9 Drawing Sheets

| CANDIDATE COMPOUND | RELATIVE FREE ENERGY DIFFERENCE (kcal/mol) | | |
|---|---|---|---|
| | EXPERIMENTAL VALUE | CALCULATION VALUE A (NOT APPLIED) | CALCULATION VALUE B (APPLIED) |
| A | 1.9 | 1.3 | 1.4 |
| B | 3.6 | 2.8 | 4.7 |
| C | 4.3 | 5.0 | 5.1 |
| D | 6.5 | 8.2 | 7.7 |

FREE ENERGY DIFFERENCE ESTIMATION METHOD AND SIMULATION APPARATUS

CROSS-REFERENCE TO RELATED APPLICATIONS

This patent application is based upon and claims the benefit of priority of the prior Japanese Patent Application No. 2011-055828 filed on Mar. 14, 2011, the entire contents of which are incorporated herein by reference.

FIELD

The embodiments discussed herein are related to a free energy difference estimation method and a simulation apparatus for calculating a free energy difference related to a binding between a macromolecular compound and a candidate compound in a solvent at higher speed.

BACKGROUND

Conventionally, molecular design is performed by using a molecular simulation. A problem of the molecular simulation is mainly the calculation amount, and a means has been provided to effectively process the calculation amount at higher speed.

For example, an electric charge determination method or the like is provided in a basis function, which is continuous for at least more than second order derivative, is applied. In the electric charge determination method, when either one grid point (or a particle) in a pair of grid points (or a pair of particles) is overlapped with a grid point in a roughly level grid which is at one level higher than the current level, an electric charge is determined for a grid point of a higher level so that an energy value of a pair in the higher level always corresponds to a proper energy value of the pair in the current level.

In drug development using a computer (computational drug development), calculation time and calculation resources cost less than a laboratory experiment. Therefore, computational drug development is simply used to comprehend a microscopic phenomenon which is not acquired by the laboratory experiment. If attempting to acquire data which are in no way inferior to the experiment, five days may be spent with approximately 320 Central. Processing Units (CPUs) for one reagent.

Patent Document 1 JP2007-80044A

SUMMARY

According to one aspect of the embodiment, there is provided a free energy difference estimation method performed in a computer to estimate a free energy difference between compounds, the method including specifying, by the computer, a change region, in which a partial free energy difference is equal to or greater than a predetermined change value, in a region of a binding constant, by referring to the partial free energy difference for each value of the binding constant indicating a bound state between a target compound and a first candidate compound bindable to the target compound, the partial free energy difference stored in a storage part; and interpolating, by the computer, the partial free energy difference of a second candidate compound in the change region, based on the partial free energy difference acquired in each of a previous region and a following region by using an approximation function.

According to other aspects of the embodiment, there may be provided a simulation apparatus for performing the free energy difference estimation method, and a non-transitory computer-readable recording medium recorded with a program which, when executed by a computer, causes the computer to perform a free energy difference estimation process.

The object and advantages of the invention will be realized and attained by means of the elements and combinations particularly pointed out in the appended claims. It is to be understood that both the foregoing general description and the following detailed description are exemplary and explanatory and are not restrictive of the invention as claimed.

DESCRIPTION OF EMBODIMENTS

In the following, embodiments of the present invention will be described with reference to the accompanying drawings. First, a binding strength of a drug candidate compound for a target protein with noncovalent binding will be described with reference to FIG. 1 and FIG. 2. The target protein is regarded as a biological functional agent concerning disease. A candidate compound is regarded as a compound which strongly binds to the target protein, and may be a compound which is considered as a drug for binding to the target protein and for blocking a function of the target protein.

Figure 1:
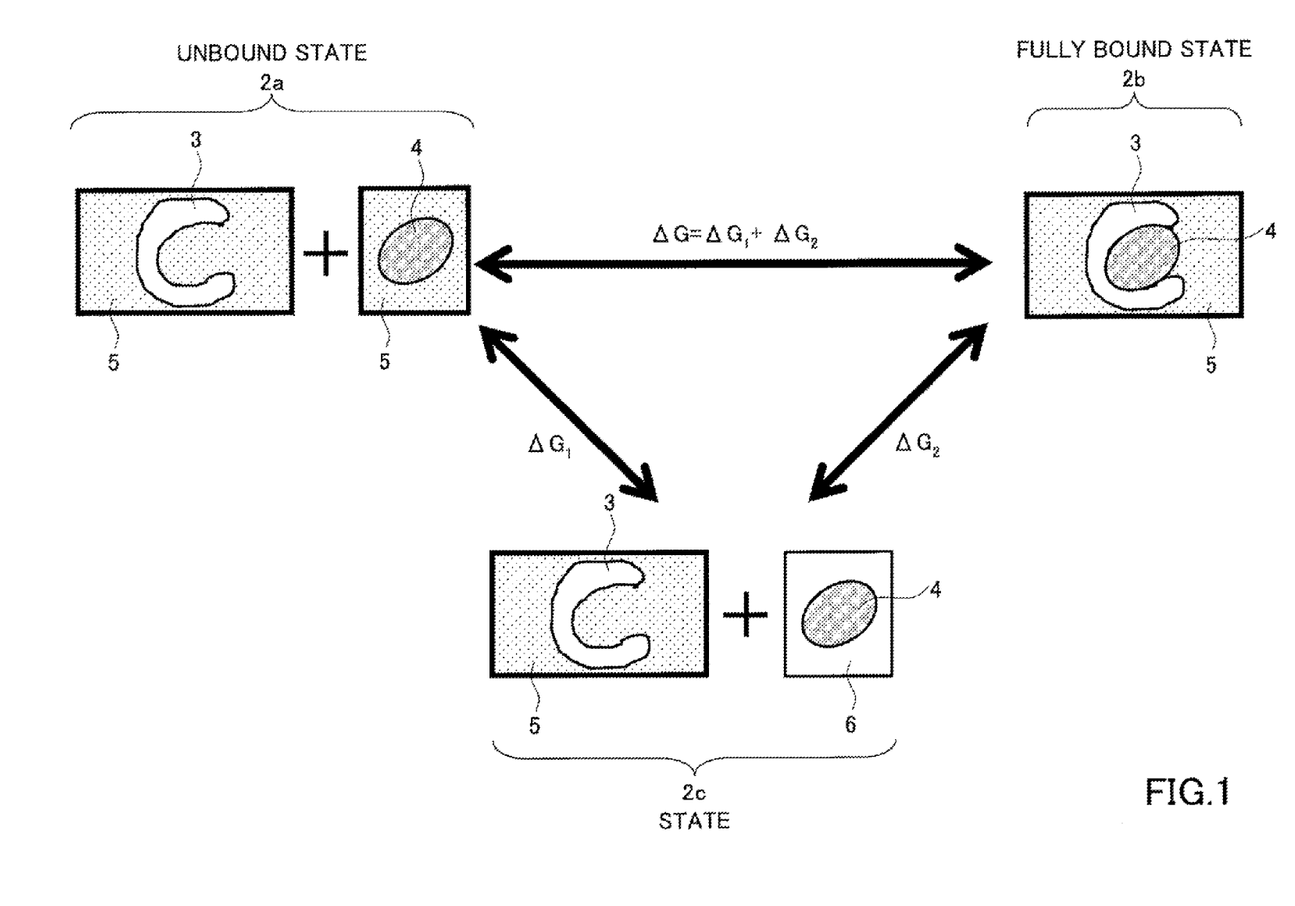
FIG. 1 is a diagram for explaining binding strength.

FIG. 1 is a diagram for explaining the binding strength. In FIG. 1, an unbound state 2a and a fully bound state 2b in water 5 (in a solvent) are illustrated. In the unbound state 2a, a target protein 3 is separated from a candidate compound 4 in the water 5. In the fully bound state 2b, the target protein 3 is bound to the candidate compound 4 in the water 5. A binding strength $\Delta G$ between the target protein 3 and the candidate compound 4 is represented by a relative free energy difference (hereinafter, simply called energy difference) between the unbound state 2a and the fully bound state 2b.

The binding strength $\Delta G$ is acquired by adding a first energy difference $\Delta G_1$ and a second energy difference $\Delta G_2$. The first energy difference $\Delta G_1$ indicates a partial energy difference between the unbound state 2a and a state 2c in which the candidate compound 4 in the water 5 is extracted into vacuum 6. The second energy difference $\Delta G_2$ indicates another partial energy difference between the fully bound state 2b and the state 2c.

Approximately 100 candidate compounds, which are narrowed down beforehand, are used as drug candidates in which the binding strength is simulated by a drug development simulator 100 applying Molecular Dynamics (MD). For one drug candidate, a simulation time of the first energy difference $\Delta G_1$ is approximately one day. On the contrary, the simulation time is approximately two weeks until a value of the second energy difference $\Delta G_2$ is converged.

Figure 2:
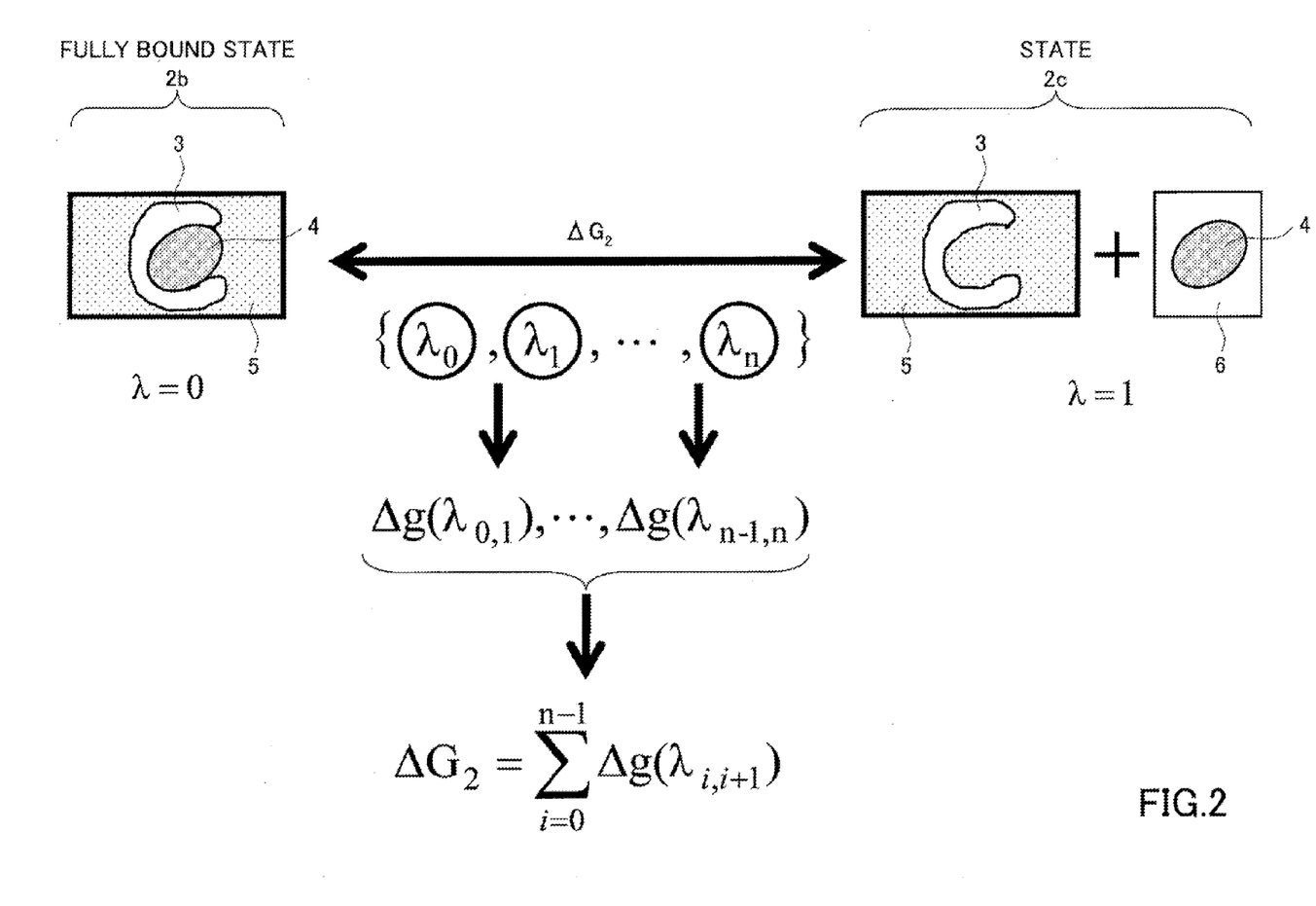
FIG. 2 is a diagram for explaining a second energy difference.

FIG. 2 is a diagram for explaining the second energy difference $\Delta G_2$. In FIG. 2, $\lambda$ indicates a binding constant. When $\lambda=0$ (zero), the target protein 3 and the candidate compound 4 are in the fully bound state 2b. When $\lambda=1$, the target protein 3 and the candidate compound 4 are in the state 2c. In other words, $\lambda$ is used as an index for representing strength of interaction between the candidate compound 4 and atoms surrounding the candidate compound 4. When $\lambda=0$, an inherent interaction is indicated. When $\lambda=1$, a state in which there is no interaction is indicated. At intervals $\lambda$ from $\lambda_0$ to $\lambda_n$ in a range of $0 \le \lambda \le 1$, an energy difference $\Delta g(\lambda_{i,i+1})$ kcal/mol (i=0, 1, . . . n−1) is calculated by using the following calculation. A total value becomes the second energy difference $\Delta G_2$.

$$\Delta G_2 = \sum_{i=0}^{n-1} \Delta g(\lambda_{i,i+1})$$

Figure 3:
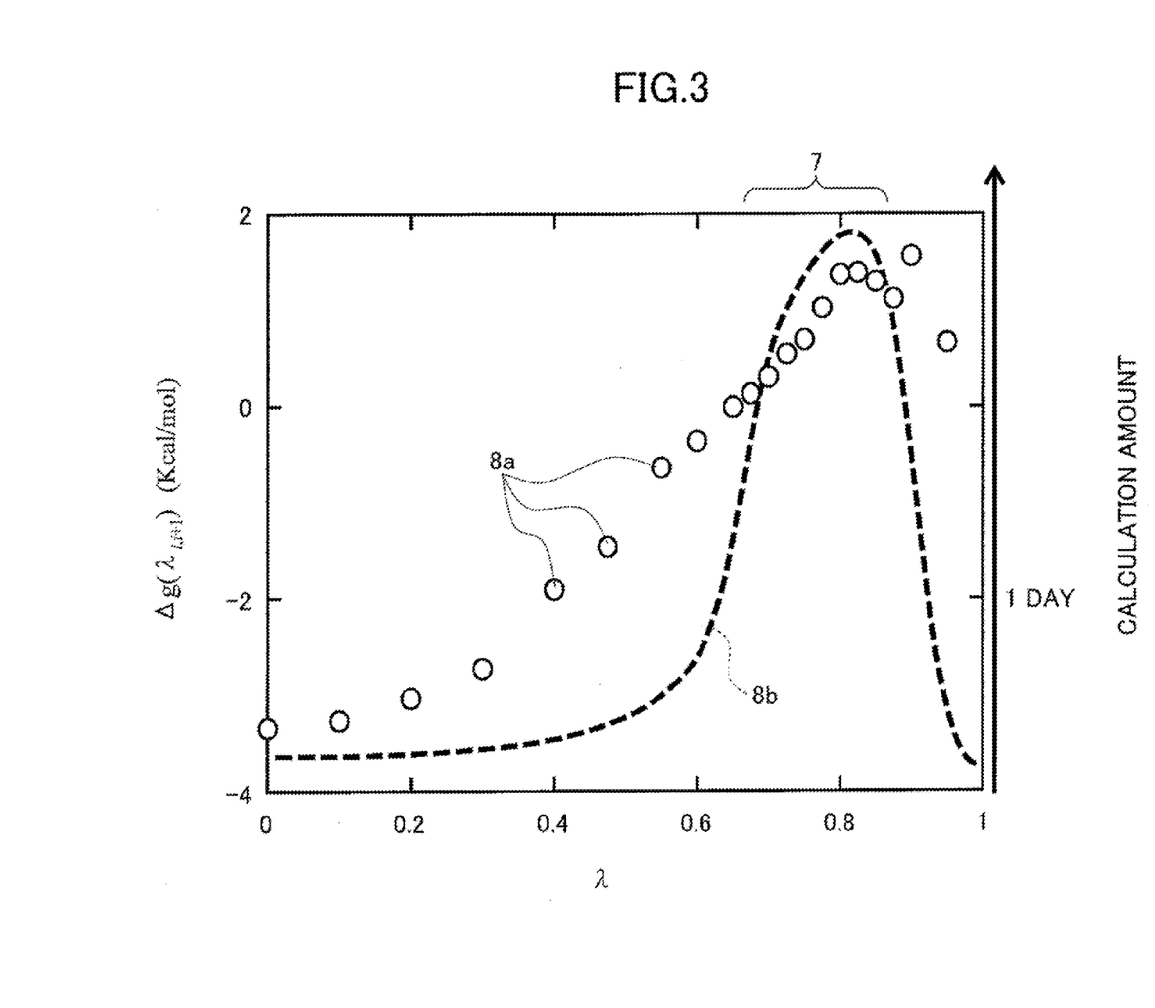
FIG. 3 is a graph illustrating a relationship between the binding strength and a calculation amount at intervals $\lambda$.

FIG. 3 is a graph illustrating a relationship between the binding strength and a calculation amount at the intervals $\lambda$. In FIG. 3, a horizontal axis indicates $\lambda$, a left vertical axis indicates the energy difference $\Delta g(\lambda_{i,i+1})$ at the intervals $\lambda$, and a right vertical axis indicates the calculation amount. The calculation amount may be either days or time spent for the calculation. Also, points 8a indicate the energy differences $\Delta g$ respective to the intervals $\lambda$, and a dashed line 8b indicates the calculation amount.

In FIG. 3, when a value of $\lambda$ is smaller than approximately 0.6, in a case of being closer to the fully bound state 2b, energy between the target protein 3 and the candidate compound 4 changes less and therefore is easily converted. Thus, approximately only one day is needed for the calculation amount. On the other hand, in a region 7 where the value of $\lambda$ is approximately 0.7 to 0.9 which is closer to the unbound state 2a, since the energy difference $\Delta g$ greatly changes, the interval may be given by $\lambda$ precisely in order to acquire an accurate calculation result. Also, in the region 7, more time is spent for convergence. Thus, a calculation time becomes significantly longer.

Figure 4:
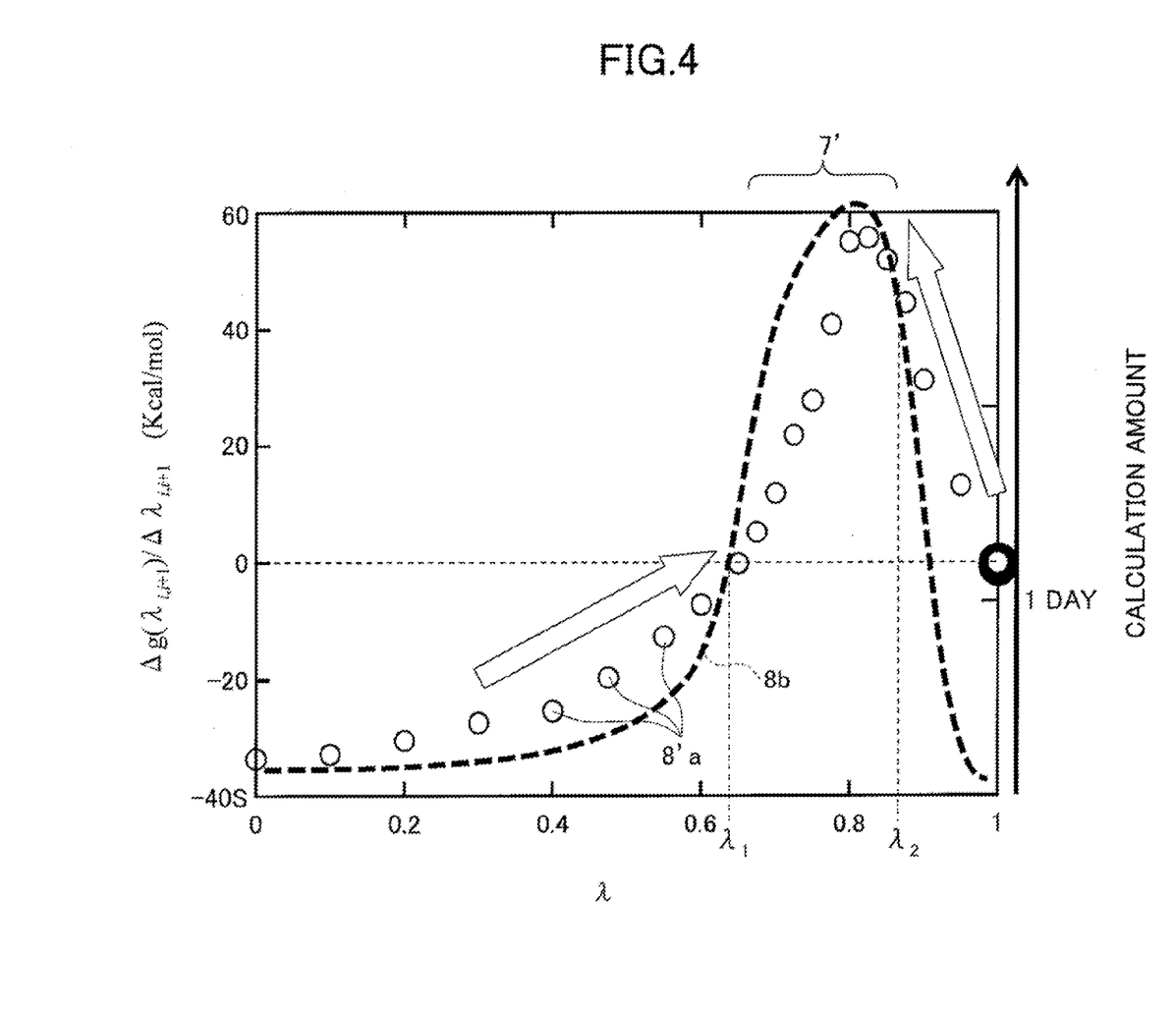
FIG. 4 is a diagram illustrating the binding strength and the calculation amount by using a differential value.
Figure 5:
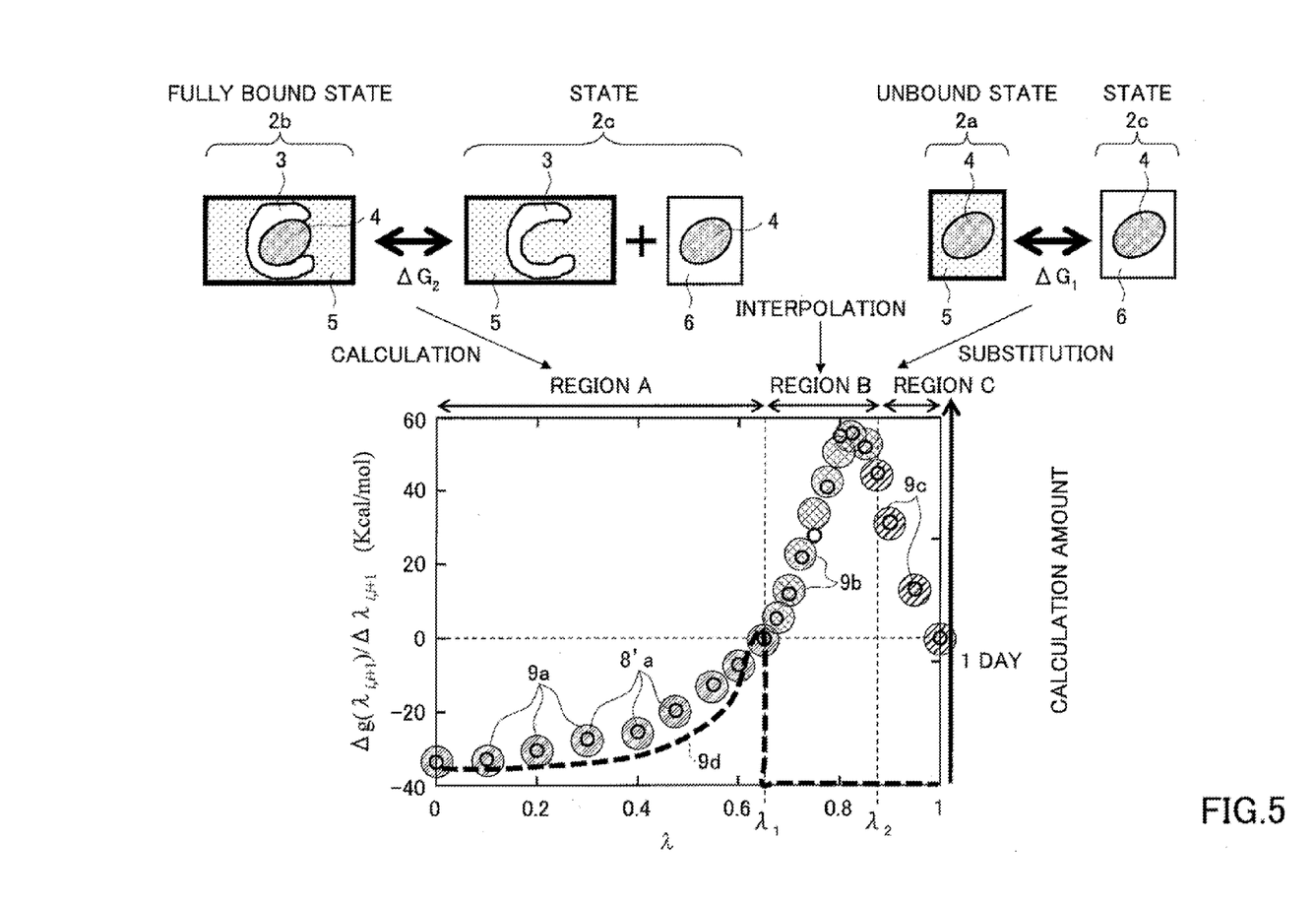
FIG. 5 is a diagram for explaining a calculation method for each of divided regions according to the embodiment.

Accordingly, the inventor has found the fact that it is possible to acquire plots depicting a smooth line, without a specific point, by representing the binding strength with a differential value $\Delta g/\Delta \lambda$, regarding the binding strength at the intervals $\lambda$ illustrated in FIG. 3, and the plot precisely indicates 0 where $\lambda=1$ (FIG. 4 and FIG. 5).

FIG. 4 is a diagram illustrating a relationship between the binding strength and the calculation amount by using the differential value. In FIG. 4, a horizontal axis indicates $\lambda$, a left vertical axis indicates a differential value $\Delta g(\lambda_{i,i+1})/\Delta \lambda_{i,i+1}$ of the energy difference $\Delta g$ at the intervals $\lambda$, and a right vertical axis indicates the calculation amount.

Referring to FIG. 4, points 8' indicate differential values $\Delta g/\Delta \lambda$ of the energy difference $\Delta g$ at the intervals $\lambda$, and form a smooth line without a specific point. Also, the plot precisely indicates 0 where $\lambda=1$. In a region exceeding the differential value 0 (zero), the calculation amount rapidly increases. The region where the calculation amount rapidly increases is regarded as a region where a calculation value is difficult to converge.

Accordingly, in the embodiment, a region of $\lambda$ is divided into three regions by using the differential value, values in a region 7', where the calculation value is difficult to converge, are estimated from values in a previous region and a following region.

FIG. 5 is a diagram for explaining a calculation method for each of the divided regions according to the embodiment. In FIG. 5, the horizontal axis and vertical axes are the same as those in FIG. 4, and the explanation thereof will be omitted. In FIG. 5, $\lambda_1$ indicates a value of $\lambda$ where the differential value becomes 0 (zero), and $\lambda_2$ indicates another value of $\lambda$ where the differential value becomes less than a predetermined value after a peak value. In the embodiment, the region from $\lambda=0$ to $\lambda=1$ is divided into a region A ($0 \le \lambda \le \lambda_1$), and a region B ($\lambda_1 < \lambda < \lambda_2$), and a region C ($\lambda_2 \le \lambda \le 1$). The region A is from $\lambda=0$ to the differential value of the energy difference $\Delta g=0$ (zero). The region B is where the differential value of the energy difference $\Delta g=0$ (zero), and continues until $\lambda=\lambda_2$ where the differential value becomes less than the predetermined value after the peak. The region C is from $\lambda=\lambda_2$ where the differential value becomes less than the predetermined value after the peak of the differential value of the energy difference $\Delta g$ to $\lambda=1$.

In the region A, the second energy difference $\Delta G_2$ between the fully bound state 2b and the state 2c is calculated. In the region C, the first energy difference $\Delta G_1$ between the unbound state 2a and the state 2c, which is calculated beforehand, is substituted, since the first energy difference $\Delta G_1$ indicates the same value as the second energy difference $\Delta G_2$. In the region B, the energy difference $\Delta g$ is approached and interpolated by using an approximation function such as a three dimensional spline or the like based on values in the region A and region C.

In the embodiment, a simulation is preformed at the intervals $\lambda$ in all regions A, B, and C for a first candidate compound, and the differential values $\Delta g/\Delta \lambda$ of the energy difference $\Delta g$ at the intervals $\lambda$. Points 8'a indicate results (the second energy differences $\Delta G_2$) from the simulation at the intervals $\lambda$ in all regions A, B, and C.

Calculations depending on the regions A, B, and C are performed from a next candidate compound. Shaded points 9a indicate the second energy difference $\Delta G_2$ in the region A. Shaded points 9c indicate the first energy difference $\Delta G_1$ between the unbound state 2a and the state 2c of the candidate compound, with which the energy difference $\Delta g$ is substituted. Shaded points 9b indicate values interpolated by using the three dimensional spline or the like from values of the region A and the region B.

Figure 6:
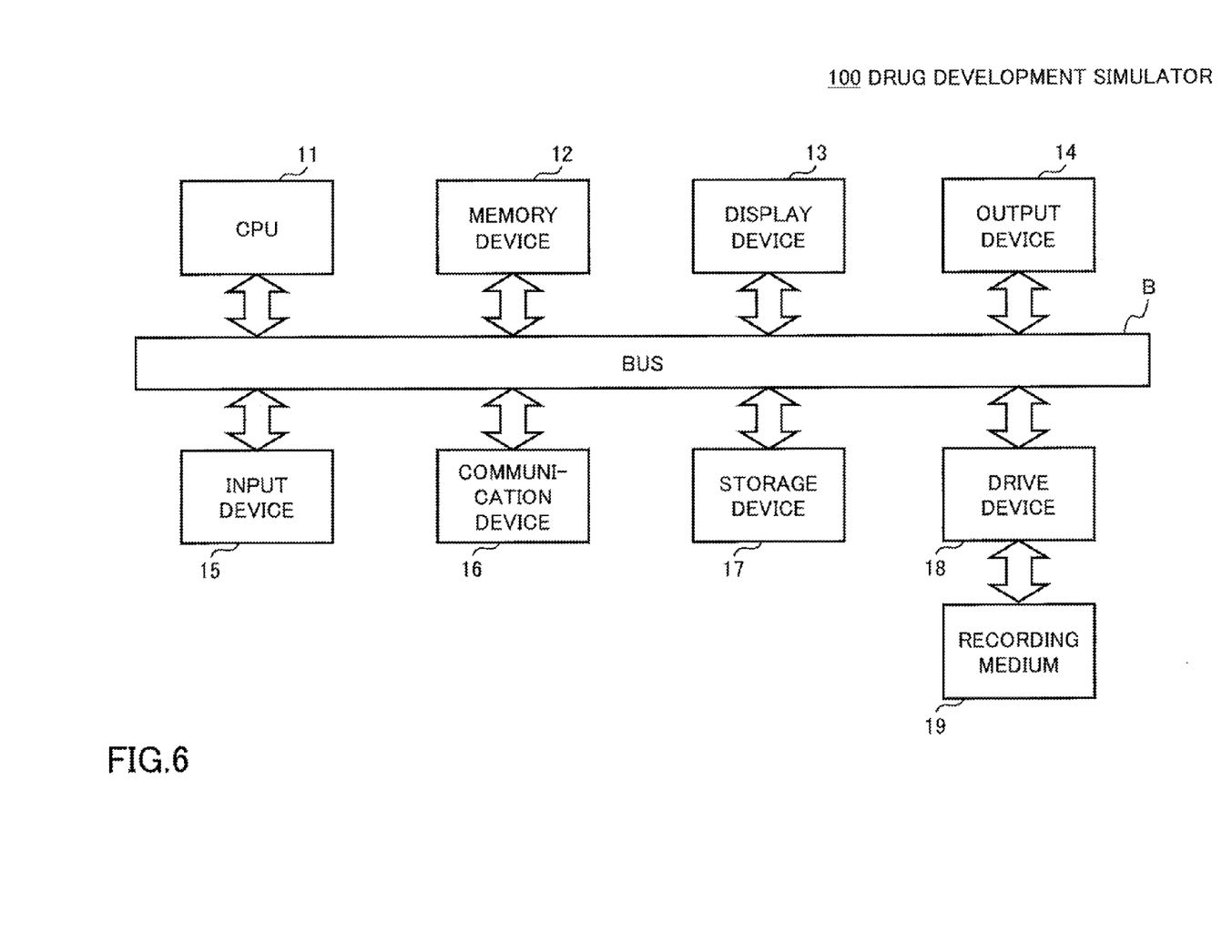
FIG. 6 is a block diagram illustrating a hardware configuration of a drug development simulator according to the embodiment.

As described above, the drug development simulator 100 for estimating a binding strength of the candidate compound for the target protein includes a hardware configuration as illustrated in FIG. 6. FIG. 6 is a block diagram illustrating the hardware configuration of the drug development simulator 100.

As illustrated in FIG. 6, the drug development simulator 100 is regarded as a terminal controlled by a computer, and includes a processor such as a Central Processing Unit (CPU) 11, a memory device 12, a display device 13, an output device 14, an input device 15, a communication device 16, a storage device 17, and a drive device 18, which are mutually connected via a bus B.

The CPU 11 controls the drug development simulator 100 in accordance with a program stored in the memory device 12. The memory device 12 includes a Random Access Memory (RAM), a Read-Only Memory (ROM), and the like, and stores the program executed by the CPU 11, data for the process by the CPU 11, data acquired in the process by the CPU 11, and the like. Also, a part of an area of the memory device 12 is assigned as a working area used in processing by the CPU 11.

The display device 13 is used to display various information items for control of the CPU 11. The output device 14 includes a printer or the like, and is used to output various information items in response to an instruction of a user. The input device 15 includes a mouse, a keyboard, and the like, and is used by the user to input various information items for the process conducted by the drug development simulator 100. For example, the communication device 16 is connected to the Internet, a Local Area Network (LAN), and the like, and is used to control communications with an external device. For example, the storage device 17 includes a hard disk unit, and stores the program and data for conducting various processes.

For example, the program for realizing the process by the drug development simulator 100 are provided to the drug development simulator 100 by a recording medium 19 such as the Compact Disc Read Only Memory (CD-ROM) or the like. That is, when the recording medium 19 storing the program is set to the drive device 18, the drive device 18 reads out the program from the recording medium 19. The program read from the recording medium 19 is installed onto the storage device 17 through the bus B. Accordingly, when the program is activated, the CPU 11 initiates the process in accordance with the program installed onto the storage device 17. It should be noted that a medium for storing the program is not limited to the CD-ROM, and any kind of a computer-readable recording medium may be used. As the computer-readable recording medium, a portable recording medium such as a Digital Versatile Disk (DVD), a Universal Serial Bus (USB) memory, a semiconductor memory such as a flash memory, or the like may be used as well as the CD-ROM.

In addition, the program for realizing the process of the drug development simulator 100 may be provided from the external device through the communication device 16.

Figure 7:
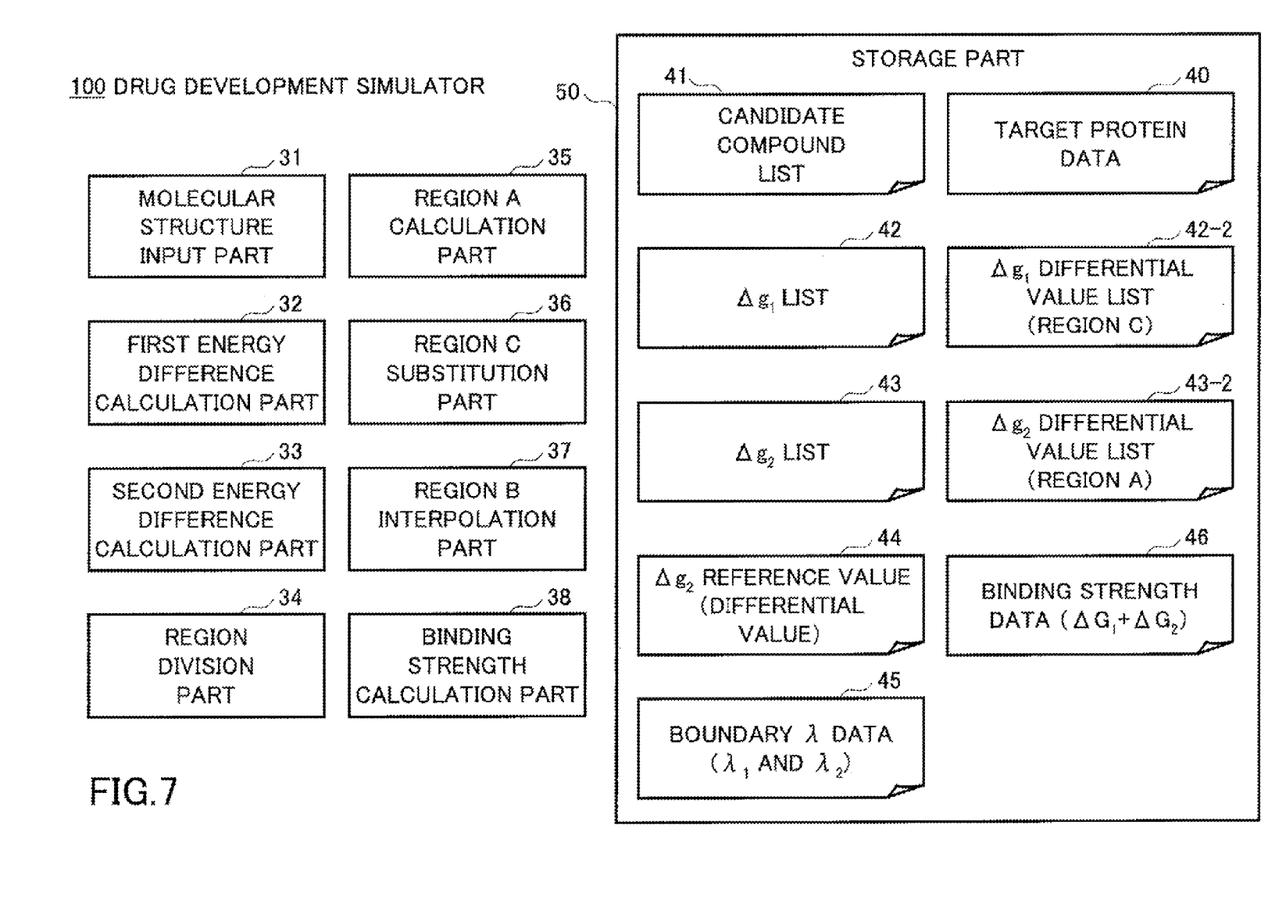
FIG. 7 is a diagram illustrating a functional configuration example of the drug development simulator according to the embodiment.

The drug development simulator 100 according to the embodiment includes a functional configuration as illustrated in FIG. 7. FIG. 7 is a diagram illustrating the functional configuration of the drug development simulator 100 according to the embodiment. In FIG. 7, the drug development simulator 100 includes a molecular structure input part 31, a first energy difference calculation part 32, a second energy difference calculation part 33, a region division part 34, a region A calculation part 35, a region C substitution part 36, a region B interpolation part 37, a binding strength calculation part 38, and the like. The parts 31 through 38 are realized by the CPU 11 executing corresponding programs.

Also, in the drug development simulator 100, target protein data 40, a candidate compound list 41, a $\Delta g_1$ list 42, a $\Delta g_1$ differential value list 42-2 for a region C, a $\Delta g_2$ list 43, a $\Delta g_2$ differential value list 43-2 for a region A, a $\Delta g_2$ reference value 44, boundary $\lambda$ data 45 for $\lambda_1$ and $\lambda_2$, and binding strength data 46 are stored in a storage part 50. The storage part 50 corresponds to a part of the memory device 12 and/or the storage device 17.

The molecular structure input part 31 inputs, by the user, a molecular structure of the target protein and the candidate compound to the drug development simulator 100. The molecular structure input part 31 is regarded as a process part which stores the target protein data 40 indicating the molecular structure of the target protein in the storage part 50, and also stores the candidate compound list 41 listing the molecular structure for identification information of each of the candidate compounds in the storage part 50.

The first energy difference calculation part 32 is regarded as a process part which refers to the candidate compound list 41, and calculates the first energy difference $\Delta g_1$ at the intervals $\lambda$ based on a macromolecular structure of the target protein indicated by the target protein data 40 and a molecular structure of each of the candidate compounds. The first energy difference $\Delta g_1$ for each of the intervals $\lambda$ corresponds to the identification information of the candidate compound and is stored in the $\Delta g_1$ list 42 in the storage part 50.

The second energy difference calculation part 33 is regarded as a process part which calculates the second energy difference $\Delta g_2$ at the intervals $\lambda$ in the entire regions A, B, and C, based on the molecular structure of a first candidate compound and the target protein data 40. The second energy difference $\Delta g_2$ calculated at the intervals $\lambda$ corresponds to the identification information of the first candidate compound and is stored in the $\Delta g_2$ list 43. Also, the second energy difference calculation part 33 calculates the differential value of the second energy difference $\Delta g_2$ of the first candidate compound at the intervals $\lambda$, and stores the differential value as a $\Delta g_2$ reference value 44 in the storage part 50.

The region division part 34 refers to the $\Delta g_2$ reference value 44, specifies $\lambda 1$ where the differential value is 0 (zero) and $\lambda 2$, and stores the boundary $\lambda$ data 45 indicating $\lambda 1$ and $\lambda 2$ in the storage part 50.

The region A calculation part 35 is regarded as a process part which calculates the second energy difference $\Delta g_2$ in the region A ($0 \leq \lambda \leq \lambda_1$) based on the molecular structure for each of the candidate compounds other than the first candidate compound, which is acquired by referring to the candidate compound list 41, and the target protein data 40. The second energy difference $\Delta g_2$ is calculated and additionally stored into the $\Delta g_2$ list 43 in the storage part 50, for each of the intervals $\lambda$ in the region A, so as to correspond to the identification information of the candidate compound. Also, the region A calculation part 35 calculates a differential value of the second energy difference $\Delta g_2$ at the intervals $\lambda$ in the region A, and stores the differential value in the $\Delta g_2$ differential value list 43-2.

The region C substitution part 36 is regarded as a process part which acquires the first energy difference $\Delta g_1$ between the candidate compound and the target protein data 40, which is calculated by the first energy difference calculation part 32, from the $\Delta g_1$ list 42, and substitutes with the first energy difference $\Delta g_1$ for the region C. The first energy difference $\Delta g_1$ acquired from the $\Delta g_1$ list 42 corresponds to the identification information of the candidate compound and is additionally stored in the $\Delta g_2$ list 43 for each of the intervals $\lambda$ in the region C. Also, the region C substitution part 36 calculates the differential value of the first energy difference $\Delta g_1$ at the intervals $\lambda$ in the region C, and stores the differential value for each interval in the $\Delta g_1$ differential value list 42-2.

The region B interpolation part 37 is regarded as a process part which refers to the differential value of the second energy difference $\Delta g_2$ for each of the intervals $\lambda$ in the region A from the $\Delta g_2$ differential value list 43-2 and the differential value of the second energy difference $\Delta g_1$ for each of the intervals $\lambda$ in the region C from the $\Delta g_1$ differential value list 42-2, and interpolates the differential value of the second energy difference $\Delta g_2$ in the region B by using the three dimensional spline or the like. The region B interpolation part 37 estimates and interpolates the differential values in the region B based on the differential values at $\lambda 1$ and $\lambda 2$ of boundaries of the region B.

Also, the region B interpolation part 37 inversely calculates the second energy difference $\Delta g_2$ at the intervals $\lambda$ in the region B from the differential value thereof being interpolated (multiplies the differential value by a respective value of $\lambda$), and additionally stores the calculated second energy difference $\Delta g_2$, which corresponds to the identification information of the candidate compound, to the $\Delta g_2$ list 43 at the intervals $\lambda$ in the region B.

The binding strength calculation part 38 is regarded as a process part which calculates the binding strength. The binding strength calculation part 38 acquires the first energy difference $\Delta G_1$ by calculating a total value for the first energy difference $\Delta g_1$ at the intervals $\lambda$ by referring to the $\Delta g_1$ list 42 for each of the candidate compounds. Moreover, the binding strength calculation part 38 acquires the second energy difference $\Delta G_1$ by calculating a total value for the second energy difference $\Delta g_2$ at the intervals $\lambda$ by referring to the $\Delta g_2$ list 43 for each of the candidate compounds. Furthermore, the binding strength calculation part 38 calculates a total of the first energy difference $\Delta g_1$ and the second energy difference $\Delta g_2$, to acquire the binding strength. The binding strength acquired by adding the first energy difference $\Delta g_1$ and the second energy difference $\Delta g_2$ is stored as the binding strength data 46 corresponding to the identification information of the candidate compound in the storage part 50. When the binding strengths are calculated for all candidate compounds listed in the candidate compound list 41, the binding strengths in the binding strength data 46 may be sorted in a descending order of the binding strength or the like and may be displayed at the display device 13 in response to a request of the user.

Figure 8:
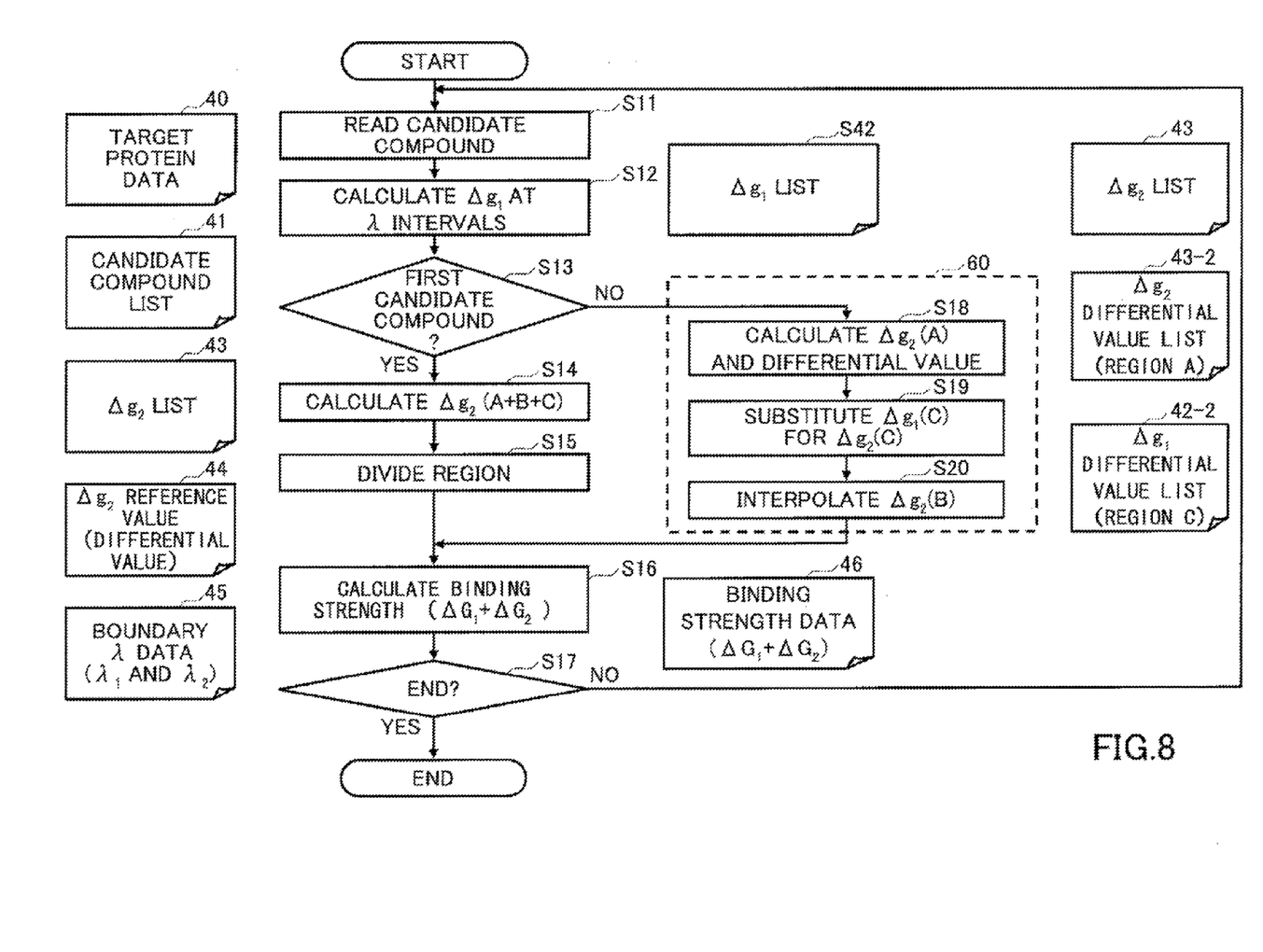
FIG. 8 is a flowchart for explaining the simulation for acquiring the binding strength, which is conducted by the drug development simulator according to the embodiment.

FIG. 8 is a flowchart for explaining the simulation for acquiring the binding strength by the drug development simulator 100. In FIG. 8, in the drug development simulator 100, the first energy difference calculation part 32 reads out a macromolecular structure of the target protein from the target protein data 40 stored in the storage part 50, and reads out the molecular structure of the candidate compound from the candidate compound list 41 (step S11), and calculates the first energy difference $\Delta g_1$ at the intervals $\lambda$ (step S12). The first energy difference calculation part 32 stores the first energy difference $\Delta g_1$ corresponding to the identification information of the candidate compound at the intervals $\lambda$ in the $\Delta g_1$ list 42 in the storage part 50.

After that, it is determined whether or not a current candidate compound is the first candidate compound (step S13). That is, it may be checked whether the current candidate compound is a candidate compound stored in a beginning of the candidate compound list 41. In a case of the first candidate compound, the second energy difference calculation part 33 calculates the second energy difference $\Delta g_2$ at the intervals $\lambda$ in the entirety of the regions A, B, and C, based on the molecular structure of the first candidate compound and the target protein data 40 (step S14). The second energy difference calculation part 33 outputs and stores the second energy difference $\Delta g_2$ at the intervals $\lambda$ in the $\Delta g_2$ list 43 in which the second energy difference $\Delta g_2$ corresponds to the identification information of the first candidate compound. Also, the second energy difference calculation part 33 calculates the differential value of each second energy difference $\Delta g_2$ in the entirety for the first candidate compound in the entirety of the regions A, B, and C, and stores the differential value of the second energy difference $\Delta g_2$ calculated at the intervals $\lambda$ to the $\Delta g_2$ reference value 44 in the storage part 50.

Next, the region division part 34 refers to the $\Delta g_2$ reference value 43 stored in the storage part 50, specifies $\lambda_1$ where the differential value of the second energy difference $\Delta g_2$ indicates 0 (zero) and $\lambda_2$ based on the differential values of the second energy difference $\Delta g_2$ at the intervals $\lambda$, and stores the boundary $\lambda$ data 45 indicating $\lambda_2$ and $\lambda_2$ (step S15).

On the other hand, in the step S13, when it is determined that the current candidate compound is the first candidate compound, the region A calculation part 35 calculates the second energy difference $\Delta g_2$ at the intervals $\lambda$ in the region A, based on the molecular structure of the candidate compound which the first energy difference calculation part 32 reads out from the candidate compound list 41 and the macromolecular structure of the target protein indicated in the target protein data 40 (step S18). The region A calculation part 35 acquires $\lambda_1$ from the boundary A data 45 and specifies the region A ($0 \leq \lambda \leq \lambda_1$). Then, the region A calculation part 35 calculates the second energy difference $\Delta g_2$ at the intervals $\lambda$ in the specified region A, and additionally stores the second energy difference $\Delta g_2$, which is corresponded to, at the intervals $\lambda$ in the region A, in $\Delta g_2$ list 43.

Also, the region A calculation part 35 calculates the differential value of the second energy difference $\Delta g_2$ at the intervals $\lambda$ in the region A, and stores the differential value calculated at the intervals $\lambda$ in the $\Delta g_2$ differential value list 43-2.

Next, the region C substitution part 36 acquires the first energy difference $\Delta g_1$ between the candidate compound and the target protein data 40, which is calculated by the first energy difference calculation part 32 for the region C, and substitutes with the acquired first energy difference $\Delta g_1$ for the region C (step S19). The region C substitution part 36 specifies the region C ($\lambda_2 \leq \lambda \leq 1$) by acquiring $\lambda_2$ from the boundary $\lambda$ data 45, and acquires the first energy difference $\Delta g_1$ of each of the intervals $\lambda$ for the specified region C from the $\Delta g_1$ list 42. The acquired first energy difference $\Delta g_1$ is corresponded to the identification information of the candidate compound and is stored in the $\Delta g_2$ list 43.

Also, the region C substitution part 36 calculates the differential value for the first energy difference $\Delta g_1$ of each of the intervals $\lambda g_1$ acquired from the $\Delta g_1$ list 42, and the differential value for each of the intervals $\lambda g_1$ in the region C to the $\Delta g_1$ differential value list 42-2.

After the differential values in the region A and the region C are acquired, the region B interpolation part 37 refers to the differential value of the second energy difference $\Delta g_2$ corresponding to $\lambda_1$ of the region A and the differential value of the second energy difference $\Delta g_2$ corresponding to $\lambda_2$ of the region C, and interpolates the differential value of the second energy difference $\Delta g_2$ in the region B by using the three dimensional spline or the like (step S20).

The region B interpolation part 37 inversely calculates the second energy difference $\Delta g_2$ at the intervals $\lambda$ in the region B from the differential value, which is interpolated by the region B interpolation part 37, of the second energy difference $\Delta g_2$ in the region B, and additionally stores the second energy difference $\Delta g_2$, which is corresponded to the identification information of the candidate compound, at the intervals $\lambda$ in the region B into the $\Delta g_2$ list 43 in the storage part 50.

After the second energy difference $\Delta g_2$ is calculated in the entirety of the region of $0 \leq \lambda \leq 1$ for the first candidate compound, and the region of $0 \leq \lambda \leq 1$ is divided into the regions A, B, and C, or after the above described processes respective to the regions A, B, and C for each of the candidate compounds other than the first candidate compound, the binding strength calculation part 38 calculates the binding strength (step S16). The binding strength calculation part 38 refers to the $\Delta g_1$ list 42 and acquires the first energy difference $\Delta G_1$ by calculating the total value of the first energy difference $\Delta g_1$ at the intervals $\lambda$. Moreover, the binding strength calculation part 38 refers to the $\Delta g_2$ list 43 and acquires the second energy difference $\Delta G_2$ by calculating the total value of the first energy difference $\Delta g_2$ at the intervals λ. Furthermore, the binding strength calculation part 38 adds the first energy difference $\Delta G_1$ and the second energy difference $\Delta G_2$ to acquire the binding strength. The binding strength calculation part 38 additionally stores the acquired binding strength, which corresponds to the identification information of the candidate compound, into the binding strength data 46 in the storage part 50.

Thus, it is determined whether the above described processes are completed for all candidate compounds listed in the candidate compound list 41 (step S17). When the processes are completed, the drug development simulator 100 terminates the simulation for acquiring the binding strength.

In step S17, when it is determined that the processes are not completed for all candidate compounds, the drug development simulator 100 goes back to the step S11 to acquire the binding strength of a next candidate compound in the candidate compound list 41.

As described above, in the drug development simulator 100, the CPU 11 executes a process 60 including the steps S18, S19, and S20 for the candidate compounds other than the first candidate compound. That is, the second energy difference $\Delta g_2$, which is a heavier process workload in the simulation, is not calculated at the intervals λ for all candidate compounds other than the first candidate compound. Therefore, it is possible to greatly reduce time spent for a simulation process.

For example, if 100 candidate compounds are targets to be processed, the second energy difference $\Delta g_2$ is calculated at the intervals λ in the entirety of the region of $0 \leq \lambda \leq 1$ in the step S14 for the first candidate compound. However, for the other 99 candidate compounds, calculations respective to the regions A, B, and C are conducted in the process 60. Accordingly, as illustrated with the dashed line 9d in FIG. 5, it is possible to omit a simulation for calculating the second energy difference $\Delta g_2$ at the intervals λ for the region B and the region C.

In a case in which the embodiment is not applied (the step S15 and the process 60 are not performed), the simulation for calculating the first energy difference $\Delta g_2$ in the step S12, which spends approximately one day for one candidate compound, is performed 100 times.

1 day×100 candidate compounds=100 days Therefore, 100 days are spent for the simulation. Also, if the simulation for calculating the second energy difference $\Delta g_2$ at the intervals λ in the step S14 is conducted 100 times, in which approximately 15 days are spent for one candidate compound.

15 days×100 candidate compounds=1500 days Accordingly, 1600 days (a total of 100 days and 1500 days) are spent.

In a case in which the embodiment is applied and performed (including the step S15 and the process 60), days spent for the simulation in step S12 are 100 days which is the same in days. However, the simulation in step S14 is conducted only for the first candidate compounds.

15 days×1 candidate compound=15 days The process 60 spending approximately one day is performed for the other 99 candidate compounds.

1 day×99 candidate compounds=99 days Accordingly, 214 days (100 days+15 days+99 days) may be spent. Compared with the case in which the embodiment is not applied, it is possible to greatly reduce the number of days for the simulation in the embodiment.

Figure 9:
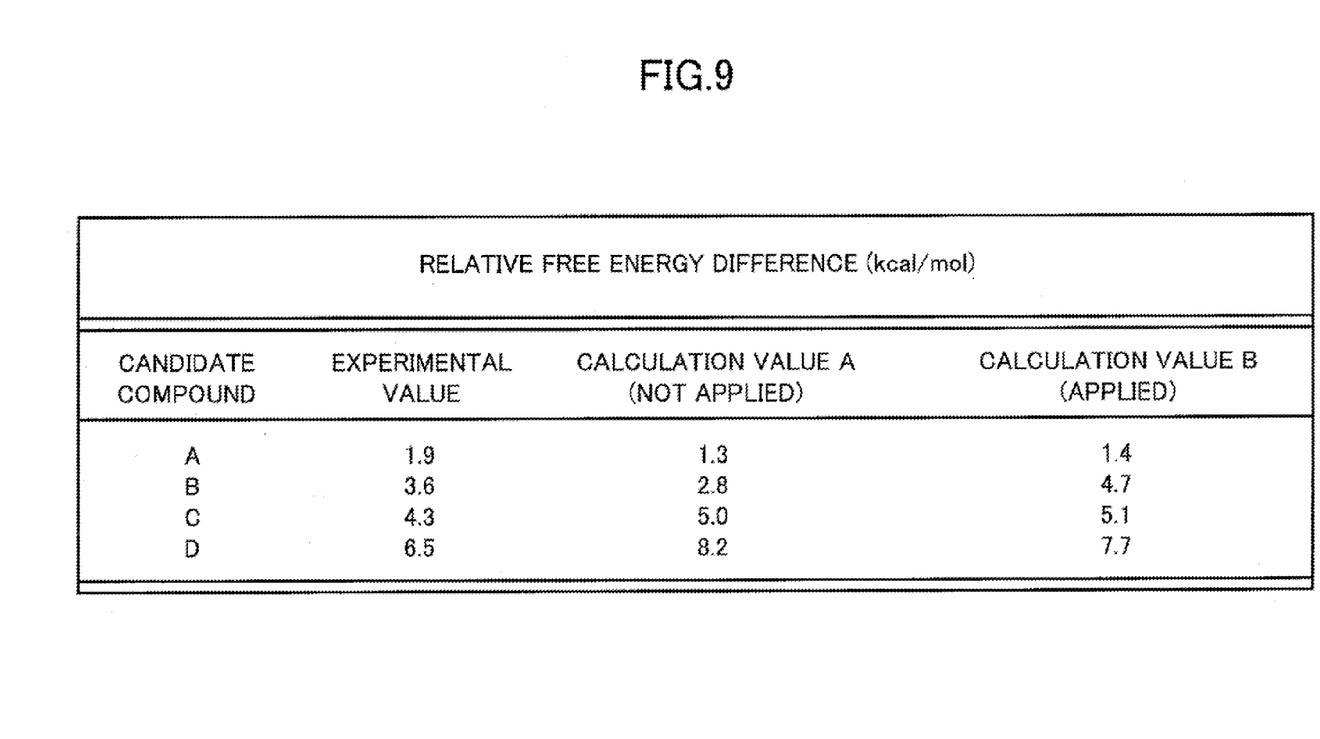
FIG. 9 is a diagram illustrating a comparison of calculation accuracy according to the embodiment.

FIG. 9 is a diagram illustrating a comparison of calculation accuracy. In FIG. 9, the binding strength between the target protein and each of candidate compounds A, B, C, and D is represented by the relative free energy difference (kcal/mol). For each of the candidate compounds A, B, C, and D, an experimental value, a calculation value A in a case in which the embodiment is not applied, and a calculation value B in a case in which the embodiment is applied are illustrated in FIG. 9.

A correlation coefficient R between the experimental value and the calculation value A indicates 0.95. The correlation coefficient R between the experimental value and the calculation value B of applying the embodiment indicates 0.98. The calculation in the embodiment improves accuracy. In the simulation by the drug development simulator 100 according to the embodiment, it is possible to calculate a free energy difference between the target protein and a drug candidate compound in the solvent at higher speed. Moreover, it is possible to similarly calculate the free energy difference between other macromolecular compounds and the candidate compounds.

As described above, in the embodiment, two states (the unbound state 2a and the fully bound state 2b) are defined by setting the binding constant λ to be a parameter. When the free energy difference between the two states is acquired by aggregating $\Delta G_i$ of interval lengths $\Delta \lambda_i$, a region (region B) where a convergence speed of the calculated value becomes slower is interpolated by using the three dimensional spline. Accordingly, it is possible to reduce days spent for the simulation, and to improve calculation accuracy.

In the embodiment, in a case in which a protein, a Deoxyribo Nucleic Acid (DNA), an Ribo Nucleic Acid (RNA), an organic compound, and the like are mutually and noncovalently bound in the solvent, it is possible to reduce computer resources for estimating the free energy difference by the simulation.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A free energy difference estimation method performed in a computer to estimate a free energy difference between compounds, the method comprising:

calculating, by the computer, a partial free enemy difference between a fully bound state and an other state, the fully bound state being when a target compound is bound to a first candidate compound, the other state being when the first candidate compound in water is extracted into vacuum;

specifying, by the computer, a first change region, a second change region, and a third change region in a region of a binding constant being from zero to one by referring to the partial free energy difference for each value of the binding constant indicating a bound state between the target compound and the first candidate compound bindable to the target compound, the partial free energy difference stored in a storage part, wherein the first change region is from where the binding constant is equal to zero to where the partial free energy difference is equal to zero, the second change region is where the partial free energy difference is equal to zero and continues until the partial free energy difference becomes less than a predetermined value after a peak, and the third change region is from where the partial free energy difference becomes less than the predetermined value after the peak to where the binding constant is one; and interpolating, by the computer, the partial free energy difference of a second candidate compound in the second change region, based on the partial free energy difference acquired in each of the first change region and the third change region by using an approximation function.

2. The free energy difference estimation method as claimed in claim 1, wherein the computer calculates the partial free energy difference related to the bound state for each value of the binding constant in the first change region, and substitutes with the partial free energy difference of the second candidate compound related to a separation from a solvent for each value of the binding constant stored in the storage part, by referring to the partial free energy difference stored in the storage part for the third change region.

3. The free energy difference estimation method as claimed in claim 2, wherein the computer calculates a first total value of a plurality of partial free energy differences by referring to the plurality of partial free energy differences which are stored the storage part and related to the separation from the solvent, calculates a second total value of a plurality of partial free energy differences related to the bound state in the first change region, the second change region, and the third change region, and calculates a relative free energy difference between the target compound and the second candidate compound by adding the first total value and the second total value.

4. The free energy difference estimation method as claimed in claim 1, wherein the computer interpolates the partial free energy difference related to the bound state by using the approximation function based on differential values of the partial free energy differences acquired for the first change region and the third change region, and acquires the partial free energy differences related to the bound state of the second change region by inversely calculating the differential values being interpolated.

5. A simulation apparatus for estimating a free energy difference between compounds, comprising:

a storage part configured to store a partial free energy difference for each value of a binding constant indicating a bound state between a target compound and a first candidate compound bindable to the target compound; and a processor configured to perform a free energy difference estimation process, wherein the free energy difference estimation process includes:

calculating the partial free energy difference between a fully bound state and an other state, the fully bound state being when a target compound is bound to the first candidate compound, the other state being when the first candidate compound in water is extracted into vacuum;

specifying a first change region, a second change region, and a third change region in a region of a binding constant being from zero to one by referring to the partial free energy difference for each value of the binding constant indicating a bound state between the target compound and the first candidate compound bindable to the target compound, the partial free energy difference stored in the storage part, wherein the first change region is from where the binding constant is equal to zero to where the partial free energy difference is equal to zero, the second change region is where the partial free energy difference is equal to zero and continues until the partial free energy difference becomes less than a predetermined value after a peak, and the third change region is from where the partial free energy difference becomes less than the predetermined value after the peak to where the binding constant is one; and interpolating the partial free energy difference of a second candidate compound in the second change region, based on the partial free energy difference acquired in each of the first change region and the third change region by using an approximation function.

6. A non-transitory computer-readable recording medium recorded with a program which, when executed by a computer, causes the computer to perform a free energy difference estimation process comprising:

calculating, by the computer, a partial free energy difference between a fully bound state and an other state, the fully bound state being when a target compound is bound to a first candidate compound, the other state being when the first candidate compound in water is extracted into vacuum;

specifying a first change region, a second change region, and a third change region in a region of a binding constant being from zero to one by referring to the partial free energy difference for each value of the binding constant indicating a bound state between the target compound and the first candidate compound bindable to the target compound, the partial free energy difference stored in a storage part, wherein the first change region is from where the binding constant is equal to zero to where the partial free energy difference is equal to zero, the second change region is where the partial free energy difference is equal to zero and continues until the partial free energy difference becomes less than a predetermined value after a peak, and the third change region is from where the partial free energy difference becomes less than the predetermined value after the peak to where the binding constant is one; and interpolating the partial free energy difference of a second candidate compound in the second change region, based on the partial free energy difference acquired in each of the first change region and the third change region by using an approximation function.

* * * * *